United States Patent [19]
Sinofsky

[11] Patent Number: 5,123,421
[45] Date of Patent: Jun. 23, 1992

[54] LIQUID ACTIVATED STEERABLE CATHETER GUIDEWIRE

[75] Inventor: Edward L. Sinofsky, Peabody, Mass.
[73] Assignee: C. R. Bard, Inc., Murray Hill, N.J.
[21] Appl. No.: 642,185
[22] Filed: Jan. 16, 1991
[51] Int. Cl.$^5$ .............................................. A61B 5/00
[52] U.S. Cl. .................................. 128/772; 128/657; 604/95
[58] Field of Search ..................... 128/657, 658, 772; 604/164, 280, 95

[56] References Cited

U.S. PATENT DOCUMENTS

| | | | |
|---|---|---|---|
| 3,470,876 | 10/1969 | Barchilon . | |
| 3,521,620 | 7/1970 | Cook . | |
| 3,773,034 | 11/1973 | Burns et al. | 128/657 |
| 3,890,977 | 6/1975 | Wilson . | |
| 4,543,090 | 9/1985 | McCoy | 128/657 |
| 4,545,390 | 10/1985 | Leary | 128/772 |
| 4,601,705 | 7/1986 | McCoy | 604/95 |
| 4,719,924 | 1/1988 | Crittenden et al. | 128/772 |
| 4,753,223 | 6/1988 | Bremer | 128/4 |
| 4,757,827 | 7/1988 | Buchbinder et al. | 128/657 |
| 4,758,222 | 7/1988 | McCoy | 604/95 |
| 4,759,748 | 7/1988 | Reed | 604/95 |
| 4,799,474 | 1/1989 | Ueda | 128/4 |

FOREIGN PATENT DOCUMENTS 3532855 3/1987 Fed. Rep. of Germany .

Primary Examiner—Max Hindenburg
Attorney, Agent, or Firm—Wolf, Greenfield & Sacks

[57] ABSTRACT

A steerable device, such as a catheter or a guidewire, adapted for insertion into a patient is provided with a means for controllably varying the curvature at the distal end of the device. The arrangement includes a conduit, at least a portion of which is formed from a material that contracts when contacted by a first liquid and expands when contacted with a second liquid. The liquids preferably are immiscible and are disposed in the conduit. Means are provided for shifting the position of the liquid column in the conduit. The portion of the conduit formed from said material is formed into a configuration that will cause that portion of the conduit to change shape depending on the position of the liquid column in the conduit.

19 Claims, 2 Drawing Sheets

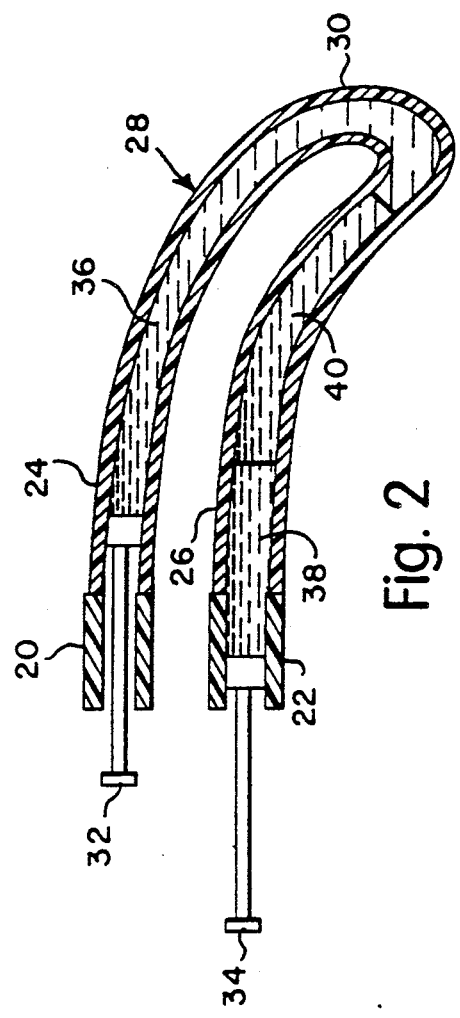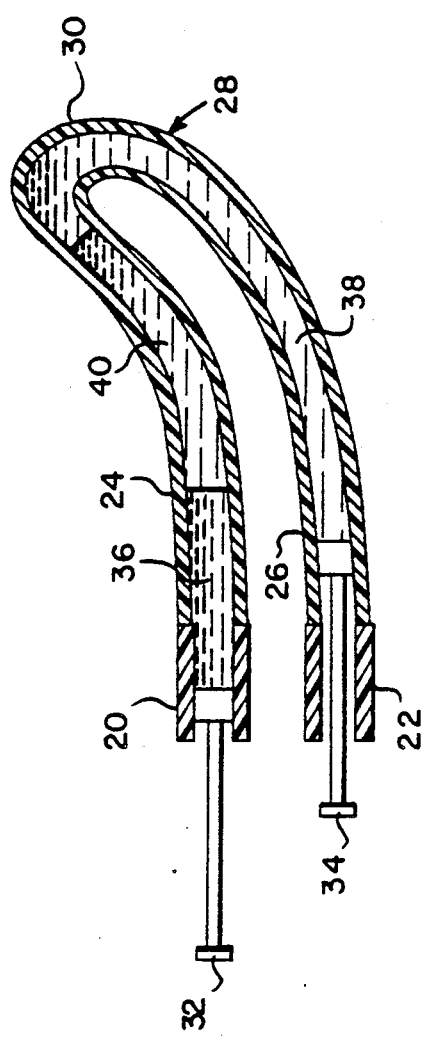

LIQUID ACTIVATED STEERABLE CATHETER GUIDEWIRE

FIELD OF THE INVENTION

This invention relates to medical catheters and guidewires used to guide such catheters.

BACKGROUND OF THE INVENTION

Catheters are used commonly in the diagnosis and treatment of a wide variety of medical conditions. A catheter typically is in the form of an elongate flexible tube adapted for insertion into the human body. In a typical procedure, the catheter is advanced and manipulated to place its distal end (the end inside the patient) at a target site in the body. The distal end of the catheter typically is constructed to perform a particular diagnostic or therapeutic procedure at that target site. For example, many catheterization procedures involve the insertion and advancement of a catheter into a patient's blood vessels. The catheter may be a diagnostic angiographic catheter intended to inject radiopaque contrast liquid into the patient's blood vessels so that they may be visualized under X-ray fluoroscopy or may be a therapeutic catheter such as a balloon angioplasty catheter in which a balloon at the distal end of the catheter is used to dilate a narrowed region of a blood vessel.

As an aid to advancement and placement of the catheter, specially constructed guidewires often are used. The guidewire may be inserted into the patient preassembled with the catheter or may be inserted into the patient independently of the catheter, with the catheter being threaded onto and advanced along the previously placed guidewire. In either case, the guidewire extends distally beyond the distal end of the catheter so that it may serve as a lead or guide for the catheter as the catheter is advanced. In order to place the distal end of the guidewire at the intended target site, the guidewire typically must be manipulated and steered through various branches of the patient's vasculature in order to reach the target site. For that purpose, it is common practice to provide a bend in the distal tip of the guidewire and to construct the guidewire so that it can transmit rotation from its proximal to its distal end. Thus, as the wire is advanced, it can be steered at branches in the vasculature by rotating it so that the bent distal tip is directed toward the intended blood vessel branch. By way of example, such guidewires are described in U.S. Pat. No. 4,545,390 (Leary). Some types of guidewires are provided with a means by which the shape of the curve at the distal end of the guidewire can be controllably adjusted from the proximal end of the guidewire without removing the guidewire from the patient. For example, U.S. Pat. Nos. 3,521,620 (Cook) and 4,719,924 (Crittenden) disclose such guidewires with controllably variable curved distal tips. Typically such guidewires include a pull wire that extends through the guidewire and is connected at its distal end to the distal tip of the guidewire. The degree to which the pull wire is pulled controls the degree of curve at the distal end of a guidewire. Such guidewires typically have a single pull wire and, therefore, can only be bent in one direction.

In some types of catheters, particularly those that are not intended to be used with a guidewire, it may be desirable to provide an adjustably curvable distal tip with control means by which the degree of curvature at the distal tip can be remotely controlled. Examples of such catheters are found, for example, in U.S. Pat. No. 4,753,223 (Brenner). Typically such catheters also use pull wires and may use a plurality of pull wires to control the direction of bending of the distal tip of the catheter. Such multiple pull wires are common in endoscopes. The use of multiple pull wires, however, requires that the diameter of the device be increased in order to accommodate the multiple pull wire arrangement. Some may use liquid pressure such as is disclosed in U.S. Pat. No. 3,773,034 (Burns et al.) to control the direction of the catheter tip.

A characteristic common to the foregoing steerable guidewires and catheters that is in order to steer and advance the device, it is necessary often to transmit torque along the length of the device, from its proximal to its distal end in order that the direction of the curve at the distal end may be controlled. In some cases, it is difficult to construct a device that will have sufficient torsional rigidity to transmit the rotation controllably, without whipping. It would be desirable, therefore, to provide a steering system for use in a guidewire or a catheter in which the distal tip of the catheter could be selectively directed within the patient's body with reduced reliance on the torsional capability of the device. It is among the general objects of the invention to provide such a device which incorporates a new approach for remotely controlling the curvature at the distal end of a guidewire or a catheter without requiring removal of the guidewire or catheter from the patient.

SUMMARY OF THE INVENTION

The invention involves the use of an element formed from a material of the type that will swell when contacted with one liquid and will shrink when contacted with another liquid. The element is incorporated into the distal tip of the guidewire or the catheter and a means is provided to selectively communicate the two types of liquids to different portions of the element. In that manner, one portion of the element may be caused to expand while the other is caused to contract, the element being configured such that the combined expansion and contraction of the different portions of the element cause it to assume a curve, the direction of the curve depending on the portions of the element to which the liquids are applied.

More particularly, the invention may incorporate a small hollow tube formed from a polyelectrolyte gel in which the tube is formed into a U-shaped configuration including a pair of legs and an arch. The U shaped element may be carried at the distal end of either a catheter or a guidewire. The polyelectrolyte is selected from a group of materials that are known to swell when contacted with certain liquids, such as water and to shrink when contacted with other liquids, for example, acetone. The liquids are immiscible (such as water and acetone). The lumen of the tube is filled with the immiscible liquids in serially alternating segments, that is, in the form of a liquid column having alternating segments of the two liquids. A means is provided for shifting the position of the liquid column through the polyelectrolyte gel tube to selectively vary the positions of the two liquids within the tube. By doing so, one of the legs of the tube may be made to be in contact with one of the liquids while the other leg is in contact with the other liquid, thus causing one leg to expand while the other contracts, thereby inducing a bend in the tube. By shifting the position of the liquid column in the tube, the positions of the liquids may be reversed with respect to the legs of the tube, thereby reversing the direction of the curve. The position of the liquid column within the tube may be controllably adjusted from the proximal end of the guidewire or catheter by syringe-like actuators or other pressure generating devices.

It is among the general objects of the invention to provide a new system for controlling the curvature at the distal end of a guidewire or catheter remotely from the proximal end.

Another object of the invention is to provide a guidewire or catheter in which the curvature at the distal end may be remotely controlled by an element, incorporated into the distal tip of the guidewire or catheter, in which the element is provided with expandable and contractable portions which may be controlled to induce a selectively directable bend in the element.

Another object of the invention is to provide a guidewire or catheter having a remotely controllable distal tip of the type described in which the element is formed from a polyelectrolyte gel that may be cause to swell or contract by contact with different, immiscible liquids.

A further object of the invention is to provide a guidewire or catheter of the type described in which the curvature at the distal tip of the device is remotely controllable without the use of pull wires.

Another object of the invention is to provide a guidewire or catheter having a remotely controllable distal tip in which the tip can be curved in at least two opposite directions.

A further object of the invention is to provide a guidewire or catheter having a remotely controllable bendable distal tip which reduces the extent to which the guidewire or catheter must be rotated in order to selectively direct the curved distal tip to selected vascular branches.

DESCRIPTION OF THE DRAWINGS

The foregoing and other objects and advantages of the invention will be appreciated more fully from the following further description thereof, with reference to the accompanying drawings wherein:

FIG. 2 is an illustration similar to FIG. 1 illustrating the distal tip of the guidewire bent in one direction; and FIG. 3 is an illustration similar to FIG. 1 but with the distal end of the guidewire bent in the opposite direction.

DETAILED DESCRIPTION OF THE ILLUSTRATIVE EMBODIMENT

Figure 1:
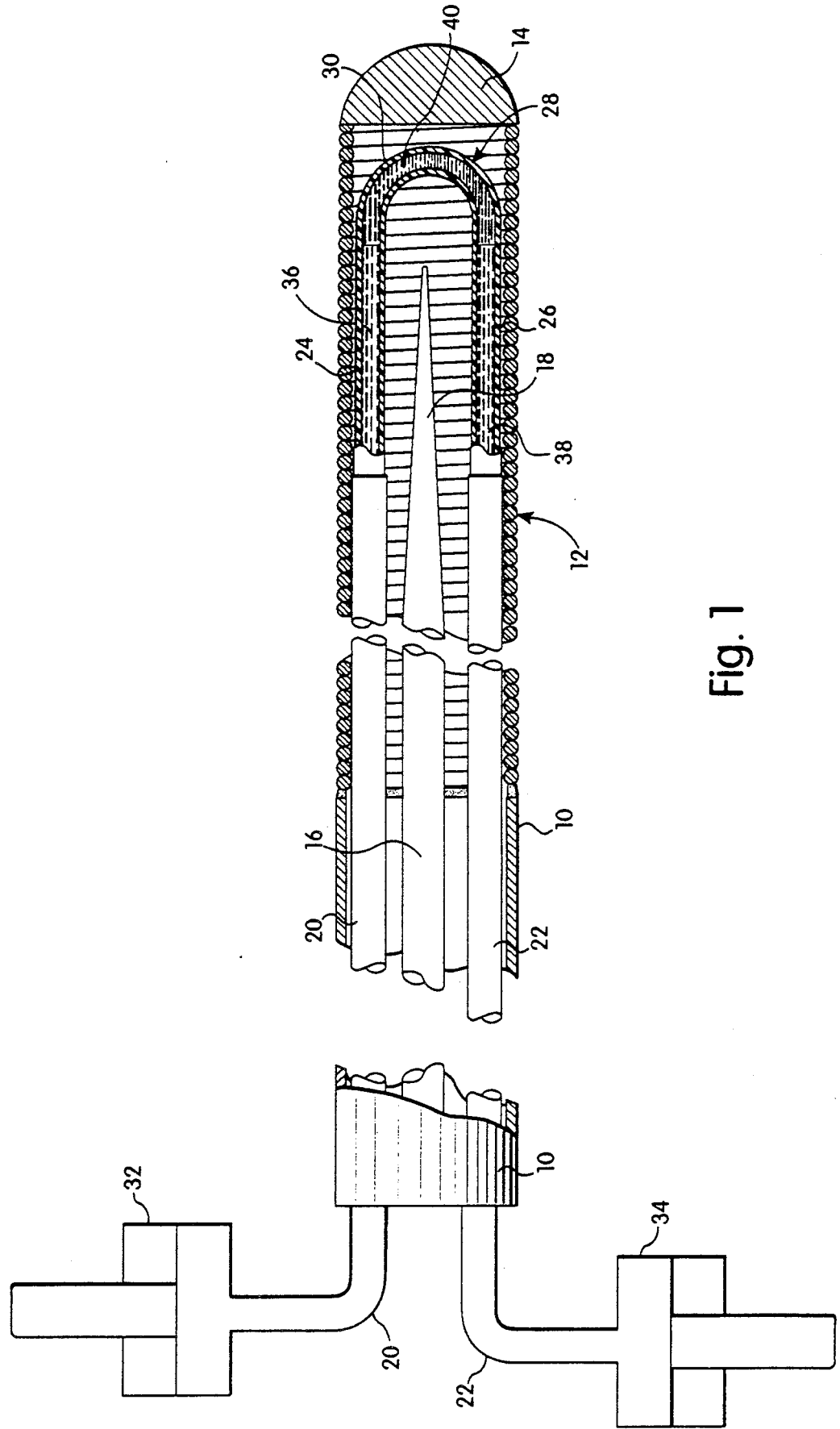
FIG. 1 is a highly schematic, diagrammatic illustration of the invention incorporated into a guidewire, illustrating the distal end of a guidewire in cross-section and in a straight configuration.

FIG. 1 illustrates the invention as incorporated in a guidewire. It should be understood, however, and will be appreciated by those skilled in the art that the principles of the invention may be incorporated into a catheter. The guidewire may be of any suitable length, depending on the length of the catheter with which it is to be used and the particular procedure and intended depth of insertion of the catheter into the patient. By way of example, guidewires typically may range in length from about 50 cm to as much as 300 cm. In the illustrative embodiment, the guidewire may include an elongate proximal tubular shaft 10 which may be formed from hypodermic tubing and which extends over the major portion of the length of the guidewire. The hypodermic tubing preferably should be adapted to transmit torque to the distal end of the guidewire. For example, in a guidewire intended for use in peripheral angioplasty, the tubular shaft 10 may be of the order of 150 cm long. The guidewire, including the tubular shaft 10 may be of the order of 0.5 mm to 1.5 mm in diameter. The distal portion of the guidewire may be formed by a helical coil 12 that is attached, at its proximal end to the distal end of the tube 10 by any appropriate means, such as brazing, soldering or the like. Preferably, the coil 12 is formed from a material that is radiopaque so that the location and shape of the distal portion of the guidewire may be monitored visually under X-ray fluoroscopy. For example, the coil may be formed from platinum, gold or alloys of such materials. A smooth hemispherical tip element 14 is attached to the distal end of the coil 12 and may be formed by a bead welded at the distal tip of the coil. The guidewire also may include a core wire 16 that extends over most of the length of the guidewire. The core wire 16 may be formed, for example, from stainless steel. It is attached at its proximal end to the proximal end of the tubular shaft 10 as by solder, welding, brazing or adhesive. The distal end of the core wire may extend well into the helical coil 12. A distal segment 18 of the core wire 16 preferably is of reduced diameter, such as a taper or the like. The reduced diameter segment 18 provides a tip having increased flexibility in a distal direction, as is commonly desirable in guidewires, to present a highly flexible non-traumatic tip. The distal tip of the core wire may terminate short of the distal tip of the coil.

In the illustrative embodiment of the invention, the guidewire includes a pair of small diameter tubes 20, 22 that extend through the tubular shaft 10 and into the distal segment of the guidewire. Connected to the distal ends of the tubes 20, 22 are legs 24, 26 of a U-shaped tube, indicated generally at 28. The legs 24, 26 are joined by an arched segment 30. The lumen defined through the tubes 20, 22 and the U-tube 28 is continuous so that liquid may flow from one of the tubes 20, 22 to the other through the U-tube 28. At the proximal end of the guidewire, the tubes 20, 22 are connected to fluid actuators 32, 34 respectively. The actuators 32, 34, which may be syringes or the like are adapted to apply pressure within tube 20, 22 selectively to cause liquid to flow in the desired direction through the conduit defined by the tubes 20, 22 and the U-tube 28.

In accordance with the invention, the U-tube 28 is formed from a material that will expand when contacted with one liquid and will contract when contacted with another liquid. For example, the tube may be formed from a polyelectrolytic gel, such as a mixture of polyvinyl alcohol and polyacrylic acid which will expand when contacted with water but which will contract when contacted with acetone. The delivery tubes 20, 22 are formed from a material that is inert to the liquids contained and may, for example, be formed from polyethylene terephthalate. The tubes 20, 22 may be attached to the legs 24, 26 of the U-tube 28 by telescoping the connected ends, one in the other, and receiving the connection with a suitable adhesive, such as a cyanoacrylate adhesive.

In the illustrative embodiment of the invention, the conduit defined by tubes 20, 22 and U-tube 28 is filled with three columnar segments of liquids including a pair of water segments 36, 38 separated by an intermediate segment 40 of suitable immiscible liquid, such as acetone. In the illustrative embodiment, the acetone causes the polyelectrolytic gel tube to contract and the water causes it to expand. As illustrated in FIG. 1, the water columns 36, 38 and the acetone segment 40 are disposed symmetrically on each side of the arch 30 and, in that configuration, the U-tube remains in a substantially straight U shaped configuration, as shown. In order to induce a bend in the shape of the each, the actuators 32, 34 are operated to shift the column of liquids within the device to locate the acetone in one of the legs and water in the other. Thus, as shown in FIG. 2 actuator 32 has been operated to shift the column of liquid to locate the acetone 40 in the leg 24 of the U-tube 28, with the other leg 26 and the arch 30 being filled with water. The leg 26 and arch 30 thus will expand while the leg 24 will contract, the differential inducing a curvature in the U-tube in the direction indicated in FIG. 2.

FIG. 3 illustrates the manner in which the device may be caused to assume a curve in the opposite direction by reversing operation of the actuators to shift the position of the liquid column, so as to place the acetone in the leg 26. The configuration of the distal end of the guidewire is such that the curvature induced in the U-tube causes the portion of the coil 12, which is highly flexible, to conform to the configuration of the U-tube, thus taking the bend induced in the U-tube.

From the foregoing, it will be appreciated that the degree and direction of curvature of the device may be controlled by selectively controlling the position of the liquid column within the U-tube. The direction may be controlled to cause the curve to bend in either direction from a straight configuration. Thus, in order to change the direction of the curve, the present invention may not require any rotation of the guidewire but, instead, may simply require operation to change the curve from one direction (as in FIG. 2) to another direction (as in FIG. 3). It should be necessary to impart some rotation to the guidewire in order to make slight adjustments to the orientation of the curved distal tip such rotational movement will be considerably less than that required with prior guidewires.

Thus, it will be appreciated that the invention provides a means by which the shape at the distal end of a guidewire or catheter may be controlled remotely by incorporating into the distal end an element having portions that are oppositely expanded and contracted thus to induce a change in shape of the element which, in turn, is imparted to the body of the guidewire or catheter. Moreover, the device may be configured so that the change in configuration may occur in opposite directions thereby enabling the device to be curved to one side or the other from a central position. Consequently, the extent to which the guidewire or catheter must be rotated, if at all, is lessened.

It should be understood, however, that the foregoing description of the invention is intended merely to be illustrative thereof and that other embodiments, modifications and equivalents may be apparent to those skilled in the art without departing from its spirit.

Having thus described the invention what I desire to claim and secure by Letters Patent is as follows.

1. An elongate flexible device adapted for insertion into the body of a patient comprising:
   an elongate shaft, at least the distal portion of which is flexible;
   a fluid flow conduit extending through the shaft and the distal portion of the shaft, at least the part of the conduit that is disposed in the distal portion being defined by a material adapted to contract when contacted with a first liquid and to expand when contacted with a second liquid;
   said conduit containing a column of liquid in alternating segments of said first and second liquids;
   the conduit being constructed and arranged to assume varying configurations depending on the position of the liquid segments in the conduit; and
   means for shifting the position of the liquid column to vary the position of said segments.

2. A device as defined in claim 1 wherein the liquids are immiscible and the segments thereof are adjacent each other.

3. A device as defined in either of claims 1 or 2 wherein said material comprises a polyelectrolyte gel.

4. A device as defined in claim 3 wherein the polyelectrolyte gel is a mixture of polyvinyl alcohol and polyacrylic acid.

5. A device as defined in claim 3 wherein the liquids comprise water and acetone.

6. A device as defined in claim 4 wherein the liquids comprise water and acetone.

7. A device as defined in claim 1 wherein the device is a guidewire.

8. A device as defined in claim 1 wherein the device is a catheter.

9. A device as defined in claims 7 or 8 wherein at least part of the fluid flow conduit in the distal portion of the device is in the form of a U-tube formed from said material, the U-tube including a pair of legs and a connecting arch.

10. A device as defined in claim 9 wherein the column of liquid includes at least three alternating segments of said liquids with a segment of one of said liquids being contained between the segments of the other of said liquids.

11. A device as defined in claim 9 wherein the device is a guidewire and the distal portion thereof is in the form of a flexible helical coil that will flex to conform to the shape of the U-tube.

12. A device as defined in claim 9 wherein the legs of the U-tubes are connected to the means for shifting the position of the liquid column by tubes inert to said first and second liquids.

13. A catheter adapted for insertion into the body of a patient comprising:
   an elongated shaft, at least the distal portion of which is flexible; 'a fluid flow conduit extending through the shaft and the distal portion of the shaft, at least the part of the conduit that is disposed in the distal portion being defined by a material adapted to contract when contacted with a first liquid and to expand when contacted with a second liquid, wherein at least part of the fluid flow conduit in the distal portion of the catheter is in the form of a U-tube formed from said material, the U-tube including a pair of legs and a connecting arch;
   said conduit containing a column of liquid in alternating segments of said first and second liquids;
   the conduit being constructed and arranged to assume varying configurations depending on the position of the liquid segments in the conduit; and
   means for shifting the position of the liquid column to vary the position of said segments.

14. A catheter as defined in claim 13 wherein the column of liquid includes at least three alternating segments of said liquids with a segment of one of said liquids being contained between the segments of the other of said liquids.

15. A catheter as defined in claim 13 wherein the legs of the U-tube are connected to the means for shifting the position of the liquid column by tubes inert to said first and second liquids.

16. A guidewire adapted for insertion into the body of a patient comprising:

an elongate shaft, at least the distal portion of which is flexible;

a fluid flow conduit extending through the shaft and the distal portion of the shaft, at least the part of the conduit that is disposed in the distal portion being defined by a material adapted to contract when contacted with a first liquid and to expand when contacted with a second liquid, when at least part of the fluid flow conduit in the distal portion of the guidewire is in the form of a U-tube formed from said material, the U-tube including a pair of legs and a connecting arch;

said conduit containing a column of liquid in alternating segments of said first and second liquids;

the conduit being constructed and arranged to assume varying configurations depending on the position of the liquid segments in the conduit; and means for shifting the position of the liquid column to vary the position of said segments.

17. A guidewire as defined in claim 16 wherein the column of liquid includes at least three alternating segments of said liquids with a segment of one of said liquids being contained between the segments of the other of said liquids.

18. A guidewire as defined in claim 16 wherein the distal portion thereof is in the form of flexible helical coil that will flex to conform to the shape of the U-shape.

19. A guidewire is defined in 16 wherein the legs of the U-tube that are connected to the means for shifting the position of the liquid column by tubes insert to said first and second liquids.

* * * * *